(12) United States Patent
Dugas et al.

(10) Patent No.: US 7,303,924 B2
(45) Date of Patent: Dec. 4, 2007

(54) METHOD OF FUNCTIONALISING SOLID SUPPORTS

(75) Inventors: Vincent Dugas, Saint Genis Laval (FR); Yves Chevalier, Irigny (FR); Eliane Souteyrand, Ecully (FR)

(73) Assignee: Centre National de la Recherche Scientifique, Ecully (FR)

( * ) Notice: Subject to any disclaimer, the term of this patent is extended or adjusted under 35 U.S.C. 154(b) by 500 days.

(21) Appl. No.: 10/483,180

(22) PCT Filed: Jul. 5, 2002

(86) PCT No.: PCT/FR02/02364

§ 371 (c)(1),
(2), (4) Date: Jun. 2, 2004

(87) PCT Pub. No.: WO03/008360

PCT Pub. Date: Jan. 30, 2003

(65) Prior Publication Data

US 2004/0209269 A1    Oct. 21, 2004

(30) Foreign Application Priority Data

Jul. 9, 2001 (FR) .................................. 01 09082

(51) Int. Cl.
*G01N 33/543* (2006.01)
*G01N 33/53* (2006.01)
*C12Q 1/68* (2006.01)
*C12M 1/34* (2006.01)

(52) U.S. Cl. .................... 436/518; 436/807; 435/6; 435/187.2

(58) Field of Classification Search ............ 435/6, 435/287.2; 436/518, 807
See application file for complete search history.

(56) References Cited

U.S. PATENT DOCUMENTS

| 5,306,853 A | 4/1994 | Pugin et al. ............... 585/269 |
| 5,565,592 A | 10/1996 | Patsidis et al. ............ 556/11 |
| 6,235,488 B1 | 5/2001 | Tom-Moy et al. ........ 435/7.5 |

OTHER PUBLICATIONS

D. Allen Annis, et al. "Polymer-Supported Chiral Co(Salen) Complexes: Synthetic Applications and Mechanistic Investigations in the Hydrolytic Kinetic Resolution of Terminal Epoxides." *American Chemical Society*. vol. 121, No. 17, 1999, pp. 4147-4154.

D. Losset, et al. "Induction Asmétrique Supramoléculaire Par Un Réactif Modéle du NADH Greffé Sur Silice." *Bull. Soc. Chim. Fr.* vol. 128, 1991, pp. 721-729.

*Primary Examiner*—Jezia Riley
(74) *Attorney, Agent, or Firm*—Morgan, Lewis & Bockius LLP

(57) ABSTRACT

The invention relates to: a method of functionalizing solid supports; the functionalized solid supports thus obtained; and the use thereof, in particular for the immobilization of biological molecules, such as nucleic acids, polypeptides, lipids, carbohydrates and hormones.

33 Claims, No Drawings

METHOD OF FUNCTIONALISING SOLID SUPPORTS

The present invention relates to a method of functionalizing solid supports, to the functionalized solid supports obtained using such a method, and to uses thereof, in particular for immobilizing biological molecules, such as nucleic acids, polypeptides, lipids, carbohydrates and hormones.

The supports carrying immobilized biological molecules are advantageously used for detecting and recognizing biological species, but other applications of these supports, such as chemical synthesis or modification on a support or else re-enhancement of biological reactions on a support, are also possible.

In the particular context of the detection and the recognition of biological species, it is essential to have functionalized solid supports exhibiting a certain number of qualities.

These supports must in particular allow reproducible immobilization of the biological molecules of interest, since reproducible immobilization is a condition of detection which is itself reproducible.

These supports must also allow immobilization of the biological molecules of interest in a sensitive manner. The sensitivity of a functionalized solid support depends on the amount of immobilization and on the method for detecting a signal, but also and especially on the background noise level (nonspecific signal). A decrease in background noise improves the signal/noise ratio. In fact, in a device in which the presence of biological species is detected close to the surface, the background noise comes essentially from the nonspecific absorption of molecules other than the biological molecules of interest whose immobilization is desired, and which should, consequently, be limited.

Furthermore, it is important to have reusable functionalized solid supports. In fact, most of the functionalized supports currently available are described as disposable, which can of course be considered an advantage by the user. However, these supports are disposable because it is quite simply not possible to use them several times, in particular due to the substantial drift of the signal measured. The term "disposable" then becomes synonymous with "mediocre quality". The possibility of having a reusable support is of great advantage since it permits the analysis of several biological samples with one and the same device, which makes it possible to perform quantitative comparisons. In addition, reusable supports allow several measurements to be made on the same sample and thus make it possible to improve the results from a statistical point of view, which cannot be envisioned with a disposable support which drifts too rapidly due to the poor immobilization of the biological molecules on the support.

Finally, on a functionalized support on which it is desired to locate the immobilized species precisely on plots, the immobilization step must be carried out in a clearly localized and homogeneous manner on the surface of the plots, in order to avoid any risk of smears or rings.

The immobilization of biological molecules on solid supports is generally carried out in two different steps:

a first step comprising functionalization of the supports, which consists of chemical modification of their surface by grafting synthetic molecules (coupling agents) which will ensure attachment of the biological molecules to the support;

a second immobilization step consisting in establishing a covalent bond between the biological molecules and these functionalized supports.

In order to establish such covalent bonds, various types of reactions may be established, depending on the nature, firstly, of the coupling agent and, secondly, of the biological molecule to be immobilized.

Thus, as regards the attachment of proteins or of oligonucleotides (bearing an amino spacer arm), the reaction with the surface involves amine functions. The surface attachment of such functions is provided mainly by bonds of the thiourea or amide type. The formation of thioureas has in particular been described in the article by Z. Guo et al., Nucleic Acid Research, 1994, 22, 5456-5465 and consists in activating aminated surfaces with sulfur-containing molecules such as, for example, phenylenediisothiocyanate, and then in reacting the molecules on the surface thus activated. The formation of amide bonds is obtained by reaction of amines with carboxylic acids, in general by chemical modification of an aminated support (for example with succinic anhydride or a polymerization reaction) as is described, for example, in U.S. Pat. Nos. 5,919,523, 5,667,976 and 6,043,353.

Direct functionalization on a solid support with carboxylic acids can be carried out by the formation of self-assembled layers of alkanethiol acids on deposits of gold (M. BONCHEVA et al., Langmuir, 1999, 15, 4317-4320; E. HUANG et al., Langmuir, 2000, 16, 3272-3280) or else by hydrosilylation reactions on silicon supports (T. Strother et al., J. Am. Chem. Soc., 2000, 122, 1205-1209); however, in the latter case, the attachment of the biomolecules involves complexation reactions.

In the particular case of the immobilization of proteins, it has already been proposed to functionalize supports made of quartz with a silane carrying ester groups which are then deprotected (J. D. Brennan et al., Can. J. Chem., 1994, 72, 721-728).

The chemical modification of biological molecules has also made it possible to develop other methods of immobilization. Thus, a method of electrochemical immobilization has been proposed, based on the polymerization of pyrrole (T. Livache et al., Biosensors & Bioelectronics, 1998, 13, 629-634 and F. Garnier et al., Synthetic Metals, 1999, 100, 89-94). This method makes it possible to immobilize molecules (oligonucleotides, peptides) carrying pyrrolyl residues by localized attachment, but necessitates the use of conducting supports and requires a method of multiplexed addressing.

It has also been proposed to modify oligonucleotides with a dialdehyde group in order to allow their attachment to hydrazide functions (D. Proudnikov et al., Analytical Biochemistry, 1998, 259, 34-41 and S. Dubiley et al., Nucleic Acid Research, 1997, 25, 2259-2265). The functionalized supports are, in this case, polyacrylamide gels or nitrocellulose gels, which form thick and therefore three-dimensional networks which have the advantage of increasing, for the same surface area, the density of the immobilized strands. However, these gels exhibit some limits with regard to the size of the plots deposited and the size of the DNA strands which can be hybridized (G. Yershov et al., Proc. Natl. Acad. Sci. USA, 1996, 93, 4913-4918).

Finally, an approach which is increasingly used involves the reaction of oligonucleotides carrying a spacer arm ending in a thiol function with surfaces functionalized with haloacetates (U.S. Pat. No. 5,412,087 and K. Tang et al., Proc. Natl. Acad. Sci. USA, 1999, 96, 10016-10020). The establishment of disulfide bridles or of thioether bonds, after addition of a pyridylsulfide group to the oligonucleotide (WO 99/20640), is possible on surfaces functionalized with thiols. Although thiols appear to be quite reactive and insensitive to humidity, these functions are however delicate to use since they have a tendency to oxidize to disulfide. A prior reduction of the disulfide in situ is therefore often necessary if reproducible results are to be obtained.

Consequently, a wide range of possibilities therefore exists for producing functionalized supports which allow the immobilization of biological molecules of interest. However, to date, it has not been possible to obtain, in a completely satisfactory manner, reusable functionalized solid supports which allow the immobilization of biological molecules of interest in a reproducible and sensitive manner, and the detection of a signal by limiting the signal/noise ratio.

For this reason, the inventors have given themselves the aim of producing such supports and have developed what forms the subject of the present invention.

A first subject of the present invention is a method of functionalizing a solid support comprising, at the surface, hydroxyl or hydride functions comprising the following steps:

a) grafting by covalent attachment (silylation or hydrosilylation) at least one bifunctional molecule comprising a protected carboxylic acid function of formula (I) below:

A—X—COOR    (I)

in which:

A represents a group which allows the covalent attachment of the bifunctional molecule of formula (I) to the hydroxyl or hydride functions of the support, R represents a group for protecting the carboxylic acid function, X represents a saturated or unsaturated, linear or branched $C_2$-$C_{18}$ hydrocarbon-based chain, optionally interrupted with one or more hetero atoms chosen from N, O and S;

b) deprotecting the carboxylic acid functions which were not deprotected during the grafting step a);

characterized in that step a) is carried out at a temperature of between 50 and 200° C. with a compound of formula (I) in which A is a monofunctional group, and in that said method also comprises a step c) of passivation of the residual hydroxyl or hydride functions of the support which have not reacted with said molecule(s) of formula (I).

According to the invention, the hydrocarbon-based chain of the bifunctional molecule of formula (I) comprises from 2 to 18 carbon atoms; such a chain length (less than 20 carbon atoms) does not make it possible to produce a solid support comprising an organized self-assembled monolayer (SAM). In fact, according to A. ULMAN, Chem. Rev., 1996, 96, 1533-1554, the formation of a SAM on solid supports by means of organosilicon compounds comprising a trifunctional end (of the alkyltrichlorosilane type) is possible when the hydrocarbon-based chain contains at least 20 carbon atoms.

On the contrary, according to the invention, the use of molecules of formula (I), in which the group A allowing the attachment of said molecules to the support is monofunctional, makes it possible to obtain dense monomolecular or submonomolecular layers in a reproducible manner. In addition, the molecules of formula (I) which are attached at the surface of the support each have their point of anchorage directly on the surface, unlike bifunctional or trifunctional molecules, which often result in grafted layers which are thick, rough and poorly defined.

The solid supports which can be functionalized according to this method are organic surfaces (plastic materials) or inorganic surfaces, preferably porous or flat, of the type such as metal oxides, silica and its derivatives (glass, quartz, etc.), i.e. any surface which exhibits hydroxyl functions at the surface, and also semiconductors of the silicon type exhibiting hydrides at the surface (Si—H).

The monofunctional group A can in particular be chosen from dialkyl(dialkylamino)silane, dialkylhalosilane, diphenyl(dialkylamino)silane, diphenylhalosilane, [(monoalkyl), (monophenyl), (dialkylamino)]silane, [(monoalkyl), (monophenyl), (halo)]silane, alkene, alkyne groups and organometallic compounds such as organomagnesium compounds or organolithium compounds.

The protective group R of the molecules of formula (I) above can be chosen from the groups described in *Protective groups in organic synthesis* (T. W. GREENE et al., 2nd edition, Wiley Interscience), such as, for example, a $C_1$-$C_4$ alkyl radical or a cyclic radical.

According to an advantageous form of this method, and when the surface of the solid support exhibits hydroxyl functions at the surface, the molecules of formula (I) are preferably chosen from the organosilicon compounds of formula (Ia) below:

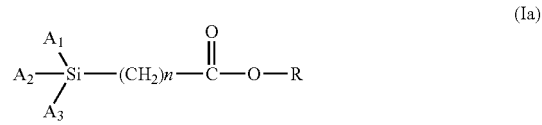

in which:

$A_1$ and $A_2$, which may be identical or different, represent a $C_1$-$C_4$ alkyl radical or a phenyl group, $A_3$ represents a $C_1$-$C_4$ alkoxy radical, a ($C_1$-$C_4$) dialkylamino radical, or a halogen atom such as chlorine, R represents a protective group chosen from $C_1$-$C_4$ alkyl radicals and cyclic radicals such as a benzyl radical, n is an integer between 2 and 18.

Among the $C_1$-$C_4$ alkyl radicals defined for $A_1$ and $A_2$, mention may in particular be made of methyl, ethyl, propyl and butyl radicals, a methyl radical being particularly preferred.

Among the ($C_1$-$C_4$) dialkylamino radicals defined for $A_3$, mention may in particular be made of a dimethylamino radical.

Among the $C_1$-$C_4$ alkyl radicals defined for the group R, mention may in particular be made of methyl, ethyl, isopropyl and tert-butyl radicals, a tert-butyl radical being particularly preferred.

According to the invention, the compounds of formula (Ia) are more particularly chosen from those in which:

$A_1$ and $A_2$, which are identical, represent a methyl radical, $A_3$ represents a dimethylamino radical or a chlorine atom, n=10, and R represents a tert-butyl radical.

In the particular case where $A_3$ represents a dimethylamino radical, the corresponding molecule (($CH_3$)$_2$N—Si($CH_3$)$_2$—($CH_2$)$_{10}$—C—(O)—O-tert-butyl), which is not commercially available, can be prepared according to conventional methods of esterification of undecylenic acid (B. M. Trost et al., "*Comprehensive organic synthesis*", 1991, 6, Pergamon Press; H. A. Staab et al., "*Azolides in organic*

*synthesis and biochemistry*", 1998, Wiley Weinheim) and of hydrosilylation (I. Fleming, "*Comprehensive organic synthesis*", volume III, chapter 13).

According to another advantageous form of this method, and when the surface of the solid support exhibits hydride functions at the surface, the molecules of formula (I) are preferably chosen from alkenes, alkynes, aldehydes, peroxides or else organometallic compounds. Among these compounds, methyl or tert-butyl esters of undecylenic acid are particularly preferred.

When step a) is a silylation step, it may be carried out both in organic or aqueous phase, which may or may not be catalyzed, and in vapor phase.

When it is carried out in organic phase, step a) advantageously comprises the following steps:
i) removal of the contaminants from the solid support and hydroxylation of its surface,
ii) introduction into a solvent chosen from nonpolar hydrocarbon-based solvents, polar solvents and mixtures thereof, under inert atmosphere, of an organosilicon compound of general formula (Ia) as defined above,
iii) silanization of the support obtained in step i) by immersion in the solution prepared in step ii) and
iv) re-curing of the silanized support obtained in step iii), after evaporation of the solvent under an inert atmosphere and at a temperature of between 50 and 200° C., preferably at 140° C., for a period of between 2 and 72 hours, and 'v) cleaning and drying of the modified support obtained in step iv).

The term "contaminants" from the solid support is intended to mean any compound such as grease, dust or the like, present at the surface of the support and which is not part of the chemical structure of the support itself.

Depending on the nature of the solid support, step i) can be carried out by means of one or more solvents and/or oxidants and/or hydroxylating agents (for example a sulfochromic mixture), of a detergent (for example Hellmanex®), of a photochemical treatment with ozone or any other suitable treatment.

In step ii), the concentration of the organosilicon compound of formula (Ia) in the solvent is preferably between $10^{-5}$ and 1 mol/liter.

When step a) is a hydrosilylation step, and when the solid support used is a support made of glass or of silica, said step a) preferably comprises the following steps:
i) removal of the contaminants from the solid support and hydration of its surface,
ii) washing of the support in an anhydrous alcohol such as anhydrous methanol,
iii) bringing the support into contact with an alkene deoxygenated beforehand under argon,
iv) hydrosilylation of the support by addition of a catalyst (Speier or Karstedt catalyst, ethyldichloroaluminum) for 2 to 24 hours at a temperature of between 90 and 200° C.

According to the invention, the grafting step a) makes it possible to attach a quantity of molecules of formula (I) between 1 and 8 µmol/m² of substrate.

Preferably, the grafting step should leave intact the protection of the carboxylic acid of the bifunctional molecule of formula (I) in order to ensure better organization of the grafted layer, the density of grafting, and also the reproducibility of the reaction. However, in some cases, deprotection of the carboxylic acid functions occurs during certain hydrosilylation reactions or when a chlorosilane is used as compound of formula (Ia).

When the grafting step a) has finished, it is therefore necessary to deprotect the carboxylic acid functions which have not been deprotected during the grafting step.

According to a first variant of the method in accordance with the invention, the deprotection step b) can be carried out under gentle conditions according to a method consisting in forming a silyl ester, which is readily hydrolyzable in water, preferably by reacting the support with a silane of formula (II) below:

$(C_1\text{-}C_4 \text{ alkyl})_3\text{—Si—Y}$      (II)

in which Y represents a halogen atom such as iodine, bromine or chlorine.

The use of a small silane molecule of formula (II) has the advantage of completing the covering of the support (passivation) since this small silane molecule also reacts with the residual hydroxyl functions of the support which have not reacted with the bifunctional molecules of formula (I) during the grafting reaction or which have formed by hydroxylation of the hydrides on the silicon during the hydrosilylation step.

The formation of these esters can be obtained:
either by reaction of the support and of an iodotrialkylsilane such as iodotrimethylsilane in an anhydrous organic solvent (such as chloroform or dichloromethane) at ambient temperature or by heating to a temperature of approximately 60° C.,
or by reaction of the support and of chlorotrimethylsilane in the presence of sodium iodide in anhydrous acetone or acetonitrile at ambient temperature or at approximately 40° C.

In this case, the passivation step c) is therefore carried out simultaneously by step b).

According to a second variant of the method in accordance with the invention, step b) is a thermal deprotection. This method of deprotection is applicable to certain carboxylic acid esters such as isopropyl and tert-butyl esters.

This thermal deprotection can be carried out by treatment of the functionalized support at a temperature of between 250 and 280° C. for 30 to 60 minutes, in an inert atmosphere (argon or nitrogen, for example).

This thermal deprotection step, carried out after the silylation or hydrosilylation step, makes it possible to generate, in situ, by simply raising the temperature, the surface carboxylic acid function.

Advantageously, this thermal deprotection step can therefore be carried out simultaneously with step a), by simply raising the temperature at the end of step a).

Also advantageously, the thermal deprotection can be carried out in a localized manner, by increasing the temperature locally, for example by means of a laser beam or of any other suitable means, so as to define activatable zones surrounded by zones in which the carboxylic acid functions remain protected.

According to the invention, the deprotection of the carboxylic acid functions is preferably carried out by formation of a silyl ester, since this method makes it possible both to generate carboxylic acid functions under gentle conditions and to block the residual hydroxyl functions of the support (support passivation step), which subsequently makes it possible to limit the nonspecific adsorption of the molecules to the support. It is in fact the nonspecific adsorption of the biological molecules which is responsible for the background noise during the detection.

Consequently, when the deprotection of the carboxylic acid functions is carried out thermally, the passivation step of the hydroxyl or hydride functions of the support is then carried out by, for example, reacting said support with a silane of formula (II) as described above or by any other conventional method known to those skilled in the art, such as, for example, by reaction of the support with hexamethyldisilazane, or else according to a method of strong adsorption of small molecules such as methanol.

When the deprotection steps of the carboxylic acid functions and passivation of the support are finished, the functionalized supports are washed with water and dried, for example, with a jet of compressed air.

A subject of the invention is also the functionalized solid support obtained using the method of functionalization in accordance with the invention and as described above.

These functionalized supports allow the reproducible immobilization of biological molecules of interest while at the same time limiting the nonspecific adsorption of molecules and therefore increasing the signal/noise ratio during detection. They also make it possible to limit the smears and rings of localized deposits by controlling the spreading of the drops of reagents.

These functionalized supports can in particular be used for immobilizing, by covalent attachment, biological molecules of interest carrying amino or hydroxyl functional groups, such as nucleic acids, polypeptides (proteins, enzymes), lipids, carbohydrates or hormones.

For the purpose of the present invention and in the remainder of the text, the term "nucleic acids" is intended to mean both oligonucleotides and DNAs or RNAs, or else nucleic acids with a modified backbone or with modified bases, such as peptide nucleic acids (PNAs), which involve peptide bonds in place of phosphodiester bonds.

A subject of the present invention is therefore also a method of immobilizing biological molecules on a functionalized solid support, characterized in that it comprises the following steps:
a) preparing a functionalized solid support comprising terminal carboxylic acid functions in the form of an ester, according to the method as defined above,
b) deprotecting and activating the terminal carboxylic acid functions,
c) bringing the modified solid support obtained in step a) or b) into contact with one or more locally applied solutions, in one or more solvents, of the biological molecule(s) to be immobilized, said biological molecules carrying at one of their ends an amine function or a hydroxyl function or a spacer arm functionalized with a primary amine function,
d) evaporating the solvent in order to bring about covalent attachment of the biological molecule(s) at the level of the carboxylic acid functions,
e) inactivating the activated carboxylic acid functions which have not reacted with the biological molecules, by means of an amine in gas phase or in solution, and
f) washing the solid support on which said biological molecules are immobilized.

The carboxylic acid function activation step b) may, for example, be carried out using a solution of N-hydroxysuccinimide, of carbonyldiimidazole or of carbodiimide, or else of any other suitable activating reagent known to those skilled in the art.

By way of example, this activation step may be carried out in the presence of carbonyldiimidazole (0.1M) in anhydrous tetrahydrofuran (THF), over approximately two hours at ambient temperature. This type of activation makes it possible in particular to obtain activated surfaces which are very reactive with respect to nucleophilic reagents (amines, alcohols, water). In this case, the biological molecules are reacted in anhydrous solvents in the presence of a tertiary amine such as triethylamine in order to ensure the presence of the amino form of the functional group of the biological molecules.

During step c), the concentration of the solution(s) of biological molecules is preferably between $10^{-6}$ and $10^{-3}$ mol/l.

During step c), it is clearly understood that, in order to solubilize the biological molecules, any aqueous or anhydrous solvent which allows good dissolution thereof and subsequent control of the evaporation of the solution could be used. The nature of the solvent will of course have to be chosen as a function of the nature of the biological molecule to be isolated. Mention may be made, by way of nonlimiting example, of phosphate buffers, dimethyl sulfoxide (DMSO), anhydrous acetonitrile or else an acetonitrile/water mixture.

Each solution of biological molecules to be immobilized can be deposited at a given place on the support, by a suitable means of microdeposition.

Thus, when the immobilization reaction is carried out under anhydrous conditions, for example in order to immobilize oligonucleotides, it is, for example, possible to use anhydrous DMSO. The reaction will of course be carried out under an anhydrous atmosphere. In this case, the oligonucleotides are preferably present in the solution at a concentration between $10^{-5}$ and $10^{-3}$ mol/l.

DNA strands and oligonucleotides are soluble in aqueous solution in any proportions. Consequently, when it is desired to immobilize this type of biological molecule, the immobilization step is preferably carried out under aqueous conditions. Activation of the carboxylic acid functions with N-hydroxysuccinimde makes it possible to carry out the procedure under aqueous conditions.

According to the invention, the immobilization step d) of the biological molecules, by evaporation of the solvent, is crucial to the correct progression of the method of immobilization, since it allows the covalent grafting of the biological molecules of interest to the functionalized support. In fact, the method of immobilization in accordance with the invention preferably uses very dilute solutions of biological molecules (of the order of $10^{-6}$ to $10^{-3}$ Mol/l), the detection of which would then be impossible if the grafting by covalent bonding was not carried out. Preferably, this evaporation step is carried out slowly, i.e. over a period of between 1 and 10 hours approximately.

When the immobilization step is finished, the activated carboxylic acid functions which have not reacted with the biological molecules are inactivated by means of an amine in gas phase or in solution (step e)).

This inactivation step makes it possible to avoid the problems of drop smearing, of contamination or of pollution during the subsequent steps, it can also be referred to as "capping".

According to an advantageous embodiment of the method of immobilization in accordance with the invention, this inactivation step is carried out by reacting, in gas phase, methylamine or dimethylamine, preferably dimethylamine, for 15 to 45 minutes.

This inactivation step can readily make it possible to treat several supports simultaneously.

According to another advantageous embodiment of this method, the inactivation step is carried out only on predefined zones of the same support, the zones which should not be inactivated being protected beforehand, for example with drops of water, of organic solvents or of mineral oil.

The deactivation of the nonprotected zones then makes it possible to create a network of activated or reactivatable zones and of chemically inert zones.

This embodiment of the method makes it possible to produce spatially resolved supports which can, for example, be obtained by depositing drops of water on a surface comprising activated carboxylic acid functions (for example with carbonyldiimidazole), followed by the inactivation step of the accessible surfaces with an amine in gas phase, and then rinsing of the support. The zones inactivated with the drops of water can then be reactivated before the step of covalent attachment of the biological molecules.

The final washing step f) is intended to desorb the molecules which have not been covalently attached to the functionalized support in accordance with the invention, in order to obtain a reproducible density of biological molecules attached at the surface.

This washing step is preferably carried out by subjecting said support to successive washing steps which are increasingly stringent, ranging, for example, from a wash with water at a temperature of approximately 80° C. for approximately one hour to a wash in a concentrated, for example 10%, aqueous solution of sodium dodecyl sulfate (SDS) at a temperature of approximately 80° C. for approximately 1 hour, optionally followed by sonication for a few minutes.

The reuse of the supports is conditioned by the obtaining of reproducible signals. This washing step performs a role as regards the reuse of these supports since it makes it possible to guarantee that the supports will not release any molecules during the optional subsequent detection steps.

Although the consequence of this washing step is to remove a certain number of biological molecules which are not covalently attached and, consequently, to decrease the amount of immobilization, and therefore the intensity of the detection signal, it also makes it possible to decrease the amount of nonspecific adsorption and therefore the background noise during detection. The overall result of this washing step is therefore an improvement in the signal/noise ratio and also in the reproducibility of the measurement.

A subject of the present invention is also the solid supports obtained using the method of immobilization in accordance with the invention, i.e. the solid supports on which the biological molecules of interest are immobilized by covalent attachment.

These solid supports can be used both as analytical tools (diagnosis, sequencing, etc.) and as tools for preparing (isolation, separation of the complex molecules) or for coating surfaces with specific properties (coating for chromatographies, "active" coatings such as antistatic coatings, antibacterial coatings, etc.).

They therefore find applications in many fields, such as:
synthesis on solid supports,
separation and purification of molecules (electrophoresis, chromatography),
in molecular biology, in particular when the biological molecules immobilized are enzymes,
as biosensors ("immunoassays", technique for analyzing DNA based on "microarrays", for example sequencing by hybridization SBH, single nucleotide polymorphism (SNP) and biomedical diagnosis).

The use of functionalized solid supports according to the invention makes it possible to immobilize various types of biological molecules and therefore to prepare various types of chips, for instance nucleic acid chips such as DNA chips, polypeptide chips such as protein chips, etc.

The use of modified solid supports according to the present invention is particularly advantageous for preparing DNA chips, i.e. supports to which a set of DNAs of known sequences is covalently attached in a quite precise order, these chips being reusable many times. Such DNA chips make it possible, by hybridization of the DNAs immobilized on the support with target nucleic acids or oligonucleotides, to determine the sequence of these target molecules or to follow gene expression. There are many applications: discovery of new genes, of new medicinal products, providing diagnoses, toxicity studies, etc.

A subject of the present invention is therefore also a nucleic acid chip or a polypeptide chip, characterized in that it is obtained by the method of immobilizing biological molecules according to the present invention, in which said biological molecules are nucleic acids or polypeptides.

The nucleic acid chips or the polypeptide chips according to the invention have the advantage of being stable and therefore of being able to be reused many times; in particular, the DNA chips can be reused in many hybridization and denaturation cycles.

Besides the above arrangements, the invention also comprises other arrangements which will emerge from the following description, which refers to an example of functionalization of the solid support, to an example of immobilization of oligonucleotides and to an example demonstrating the reproducibility of the method of immobilization in accordance with the invention.

It should be clearly understood, however, that these examples are given only by way of illustration of the subject of the invention, of which they in no way constitute a limitation.

EXAMPLE 1

Preparation of a Functionalized Solid Support

1) Cleaning and Hydroxylation of the Samples

Glass slides (76×26 mm) are immersed in a solution of sulfuric acid and hydrogen peroxide (7/3 v/v) at 80° C. for one hour. The slides are then thoroughly rinsed with ultra pure water and then dried using a gas blower. They are finally placed in a glass reactor.

2) Silanization

The reactor containing the glass slides is heated at 140° C. for one hour under vacuum and then for one hour under sweeping of dry inert gas (argon, nitrogen). The reactor is then cooled in a bath of ice-cold water and 150 ml of pentane are injected so as to cover the surface of the samples. 300 μl of silane are then injected.

The pentane is then evaporated off under vacuum and the reactor is then heated to 140° C. and swept with a stream of inert gas (argon or nitrogen) for 12 hours.

3) Rinsing of the Samples

At the end of silanization, the glass slides are washed in tetrahydrofuran (THF) under ultrasound, before being stored and being subjected to the other functionalization steps.

EXAMPLE 2

Immobilization of Oligonucleotides on a Functionalized Support in Accordance with the Invention 1) Deprotection of the Carboxylic Acid Functions The functionalized glass slides obtained above in example 1 are dried under an inert atmosphere at 140° C. for 2 hours.

After cooling, they are immersed in a solution of dichloromethane (DCM) pre-dried over alumina, and the iodotrimethylsilane is injected in an amount sufficient to reach a concentration of 0.1M. The hydrolysis is carried out overnight at ambient temperature. At the end of the reaction, the slides are washed with deionized water and dried with a jet of compressed air.

2) Activation of the Samples with N-hydroxysuccinimide

The slides are dried at 140° C. under argon for two hours. After cooling, they are immersed in a solution of anhydrous THF containing N-hydroxysuccinimide (0.1M) and diisopropylcarbodiimide (0.1M). The activation is carried out for 5 hours at ambient temperature. The slides are then rinsed with anhydrous THF and then stored under an inert atmosphere in the dark.

3) Immobilization of the Oligonucleotides

The oligonucleotides (25-mers, carrying a spacer arm functionalized with an amine function ($C_6$—$NH_2$)) are solubilized in PBS (Phosphate-Buffered Saline) phosphate buffer, pH 8.5. Surfaces of 1 cm² are covered with 50 µl of oligonucleotide solution. After slow evaporation of the PBS buffer at a temperature of 50° C., the slides are inactivated by blocking (capping) the acid functions which would have not reacted with the amine functions of the oligonucleotide spacer arms. To do this, the slides are treated with methylamine in gas phase for 30 minutes.

4) Washing of the Slides

To finish, the surfaces are washed in increasingly stringent successive baths: ultra pure water at 100° C. for 45 minutes, then 10% SDS at 80° C. for 45 minutes and, finally, 10% SDS with ultrasound for 5 minutes.

EXAMPLE 3

Demonstration of the Reproducibility of the Method of Immobilization in Accordance with the Invention Various glass slides functionalized according to the method described above in example 1 and activated with N-hydroxysuccinimide according to the method described above in example 2 were used to immobilize 1 µl of solutions of oligonucleotides at 12 µmol/l (25-mers, carrying, in the 3' position, a spacer arm comprising a primary amine function).

After washing and hybridization of the complementary sequence, the results regarding the number of strands hybridized per cm² on three different slides, after washing with 1×SSC (Saline Sodium Citrate) buffer, which is a ½₀ dilution of a 20×SSC buffer containing a mixture of NaCl (3M) and of sodium citrate (3M), at a temperature of 47° C. for 45 minutes, were as follows (quantitative data obtained by radioactive labeling with $^{32}P$):

slide No. 1: $2.20 \times 10^{10}$
slide No. 2: $2.26 \times 10^{10}$
slide No. 3: $2.23 \times 10^{10}$ These results demonstrate the great reproducibility of the method of immobilization in accordance with the invention.

On another glass slide, a first hybridization with a 60-base pair PCR double strand gave a hybridization of the order of $3.95 \times 10^8$ strand/cm². After denaturation and rehybridization under conditions identical to the previous three slides, a density of $2.6 \times 10^{10}$ oligonucleotide strands/cm² was obtained.

Consequently, this set of results demonstrates the great reproducibility of the slides between batches and also the possibility of reusing the supports without loss of signal.

The invention claimed is:

1. A method of functionalising a solid support comprising, at the surface, hydroxyl or hydride functions comprising the following steps:

a) grafting by covalent attachment at least one bifunctional molecule comprising a protected carboxylic acid function of formula (I) below:

A—X—COOR (I)

in which:
A represents a group which allows the covalent attachment of the bifunctional molecule of formula (I) to the hydroxyl or hydride functions of the support,
R represents a group for protecting the carboxylic acid function,
X represents a saturated or unsaturated, linear or branched $C_2$-$C_{18}$ hydrocarbon-based chain;

b) deprotecting the carboxylic acid functions which were not deprotected during the grafting step a); and, c) passivation of the residual hydroxyl or hydride functions of the support which have not reacted with said molecule(s) of formula (I);

wherein step a) is carried out at a temperature of between 50 and 200° C. with a compound of formula (I) in which A is a monofunctional group.

2. The method of claim 1 wherein the grafting of step a) is conducted via silanization or hydrosilylation.

3. The method of claim 1 wherein the $C_2$ $C_{18}$ hydrocarbon-based chain is interrupted with one or more hetero atoms selected from the group consisting of N, O and S.

4. The method of claim 1, wherein the solid supports are selected from the group consisting of plastic materials, metal oxides, silica and its derivatives and semiconductors.

5. The method of claim 1, wherein the monofunctional group A is selected from the group consisting of dialkyl (dialkylamino)silane, dialkylhalosilane, diphenyl(dialkylamino)silane, diphenylhalosilane, [(monoalkyl),(monophenyl),(dialkylamino)]silane, [(monoalkyl),(monophenyl),(halo)]silane, alkene, alkyne groups and organometallic compounds.

6. The method of claim 1, wherein the protective group R is a $C_1$-$C_4$ alkyl radical or a cyclic radical.

7. The method of claim 1, wherein the surface of the solid support exhibits hydroxyl functional groups at the surface and wherein the molecules of formula (I) are chosen from the organosilicon compounds of formula (Ia) below:

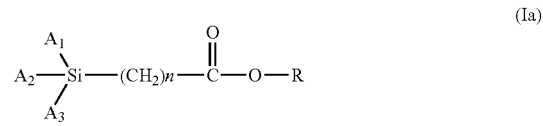

in which:
$A_1$ and $A_2$, which may be identical or different, represent a $C_1$-$C_4$ alkyl or phenyl radical,
$A_3$ represents a $C_1$-$C_4$ alkoxy radical, a ($C_1$-$C_4$) dialkylamino radical, or a halogen atom such as chlorine,
R represents a protective group selected from $C_1$-$C_4$ alkyl radicals and cyclic radicals, and
n is an integer between 2 and 18.

8. The method of claim 7, wherein the compounds of formula (Ia) are chosen from those in which:
   $A_1$ and $A_2$, are identical, and represent a methyl radical,
   $A_3$ represents a dimethylamino radical or a chlorine atom, n=10, and
   R represents a tert-butyl radical.

9. The method of claim 1, wherein the surface of the solid support exhibits hydride functional groups at the surface and wherein the molecules of formula (I) are selected from the group consisting of alkenes, alkynes, aldehydes, peroxides and organometallic compounds.

10. The method of claim 9, wherein the compounds of formula (I) are methyl or tert-butyl esters of undecylenic acid.

11. The method of claim 2, wherein step a) is a silanization step in organic phase, comprising the following steps:
   i) removing contaminants from the solid support and hydroxylating its surface,
   ii) introducing into a solvent chosen from nonpolar hydrocarbon-based solvents, polar solvents and mixtures thereof, under an inert atmosphere, an organosilicon compound of general formula (Ia),
   iii) silanization of the support obtained in step i) by immersion in the solution prepared in step ii) and
   iv) re-curing of the silanized support obtained in step iii), after evaporation of the solvent under an inert atmosphere and at a temperature of between 50 and 200° C., for a period of between 2 and 72 hours, and
   v) cleaning and drying of the modified support obtained in step iv).

12. The method of claim 11 wherein the re-curing of step iv) is conducted at a temperature of 140° C.

13. The method of claim 2, wherein the solid support is a support made of glass or of silica, and wherein step a) is a hydrosilylation step comprising the following steps:
   i) removing the contaminants from the solid support and hydration of its surface,
   ii) washing of the support in an anhydrous alcohol,
   iii) bringing the support into contact with an alkene deoxygenated beforehand under argon, and,
   iv) hydrosilylation of the support by addition of a catalyst for 2 to 24 hours at a temperature of between 90 and 200° C.

14. The method of claim 13, wherein the anhydrous alcohol of step ii) is anhydrous methanol.

15. The method of claim 1, wherein the deprotection step b) is carried out by formation of a silyl ester by reacting the support with a silane of formula (II) below:

$$(C_1\text{-}C_4\text{ alkyl})_3\text{---Si---Y} \quad \text{(II)}$$

in which Y represents a halogen atom.

16. The method of claim 15 wherein the halogen atom is iodine, bromine or chlorine.

17. The method of claim 15, wherein the formation of the silyl ester is obtained
   by reaction of the support and of an iodotrialkylsilane in an anhydrous organic solvent at ambient temperature or a temperature of approximately 60° C.

18. The method of claim 15, wherein the formation of the silyl ester is obtained
   by reaction of the support and of chlorotrimethylsilane in the presence of sodium iodide in anhydrous acetone or acetonitrile at ambient temperature or at approximately 40° C.

19. The method of claim 15, wherein step b) and step c) are carried out simultaneously.

20. The method of claim 1, wherein step b) is a thermal deprotection step.

21. The method of claim 20, wherein the thermal deprotection step is carried out simultaneously with step a), by raising the temperature at the end of step a).

22. A functionalized solid support produced by the method of claim 1.

23. A method of immobilizing biological molecules on a functionalized solid support, comprising immobilizing, by covalent attachment, biological molecules of interest carrying amino or hydroxyl functional groups onto the functionalized solid support of claim 22.

24. The method of claim 23, wherein the biological molecules are selected from the group consisting of nucleic acids, polypeptides, lipids, carbohydrates and hormones.

25. A method of immobilizing biological molecules on a functionalized solid support, comprising the following steps:
   a) preparing a functionalized solid support comprising terminal carboxylic acid functional groups in the form of an ester, according to the method of claim 1,
   b) deprotecting and activating the terminal carboxylic acid functional groups,
   c) bringing the modified solid support obtained in step a) or b) into contact with one or more locally applied solutions, in one or more solvents, of the biological molecule(s) to be immobilized, said biological molecules carrying at one of their ends an amine functional group or a hydroxyl functional group or a spacer arm functionalized with a primary amine functional group,
   d) evaporating the solvent in order to bring about covalent attachment of the biological molecule(s) at the level of the carboxylic acid functional groups,
   e) inactivating the activated carboxylic acid functional groups which have not reacted with the biological molecules, by means of an amine in gas phase or in solution, and
   f) washing the solid support on which said biological molecules are immobilized.

26. The method of claim 25, wherein the amine used in step e) is either methylamine or dimethylamine.

27. The method of claim 25, wherein step e) is carried out only on predefined zones of the same support, wherein the zones are protected beforehand to prevent inactivation.

28. A solid support produced by the method of claim 23.

29. A solid support produced by the method of claim 25.

30. The solid support of claim 28, wherein the biological molecules immobilized are nucleic acids or polypeptides.

31. The solid support of claim 29, wherein the biological molecules immobilized are nucleic acids or polypeptides.

32. The solid support of claim 30 wherein it is a size appropriate for use as a nucleic acid chip or a polypeptide chip.

33. The solid support of claim 31 wherein it is a size appropriate for use as a nucleic acid chip or a polypeptide chip.

* * * * *